(12) United States Patent
Hitchcock et al.

(10) Patent No.: US 8,695,601 B2
(45) Date of Patent: Apr. 15, 2014

(54) FOREHEAD SUPPORT FOR A PATIENT INTERFACE

(75) Inventors: Robin Garth Hitchcock, Carlingford (AU); David John Worboys, Belrose (AU); Errol Savio Alex D'Souza, Hornsby (AU)

(73) Assignee: ResMed Limited, Bella Vista (AU)

(*) Notice: Subject to any disclaimer, the term of this patent is extended or adjusted under 35 U.S.C. 154(b) by 1075 days.

(21) Appl. No.: 11/630,360

(22) PCT Filed: Jun. 24, 2005

(86) PCT No.: PCT/AU2005/000931
§ 371 (c)(1),
(2), (4) Date: Jan. 9, 2009

(87) PCT Pub. No.: WO2006/000046
PCT Pub. Date: Jan. 5, 2006

(65) Prior Publication Data
US 2011/0259337 A1    Oct. 27, 2011

Related U.S. Application Data

(60) Provisional application No. 60/582,538, filed on Jun. 25, 2004.

(51) Int. Cl.
*A62B 18/08*    (2006.01)

(52) U.S. Cl.
USPC .................................. 128/206.24; 128/207.11

(58) Field of Classification Search
USPC ............ 128/207.11, 202.27, 206.13, 206.27, 128/DIG. 26, 206.21, 206.28, 200.24, 128/206.24, 206.22, 206.23, 206.25, 128/206.26, 206.29, 207.12, 207.313
See application file for complete search history.

(56) References Cited

U.S. PATENT DOCUMENTS

| | | | |
|---|---|---|---|
| 5,558,090 A | 9/1996 | James | |
| 6,388,640 B1 | 5/2002 | Chigira et al. | |
| 6,422,238 B1 | 7/2002 | Lithgow | |
| 6,463,931 B1 * | 10/2002 | Kwok et al. | 128/207.11 |
| 6,494,207 B1 * | 12/2002 | Kwok | 128/207.11 |
| 6,532,961 B1 * | 3/2003 | Kwok et al. | 128/206.21 |
| 6,536,435 B1 | 3/2003 | Fecteau et al. | |

(Continued)

FOREIGN PATENT DOCUMENTS

| | | |
|---|---|---|
| AU | 200071882 | 6/2001 |
| DE | 19808105 | 9/1999 |

(Continued)

OTHER PUBLICATIONS

Examiner's First Report issued in Australian Appln. No. 2005256167 (Apr. 29, 2010).

(Continued)

*Primary Examiner* — Lynne Anderson
*Assistant Examiner* — Bradley Philips
(74) *Attorney, Agent, or Firm* — Nixon & Vanderhye P.C.

(57) ABSTRACT

A mask assembly includes a forehead support having a base provided to a frame and at least one, and preferably two upwardly extending support arms. The arms define a fixed or an adjustable included angle that is preferably less than 180° and, in the range of about 100°-150°. The arms can be attached either directly to headgear straps, or the arms can be connected to headgear straps via clips.

22 Claims, 12 Drawing Sheets

(56) References Cited

U.S. PATENT DOCUMENTS

| | | | |
|---|---|---|---|
| 6,595,214 B1 | 7/2003 | Hecker et al. | |
| 6,631,718 B1 * | 10/2003 | Lovell | 128/206.24 |
| 6,712,072 B1 * | 3/2004 | Lang | 128/206.27 |
| 6,886,564 B2 * | 5/2005 | Sullivan et al. | 128/206.24 |
| 6,986,352 B2 | 1/2006 | Frater et al. | |
| 7,059,326 B2 * | 6/2006 | Heidmann et al. | 128/207.11 |
| 7,779,832 B1 * | 8/2010 | Ho | 128/201.22 |
| 2003/0075182 A1 * | 4/2003 | Heidmann et al. | 128/207.11 |
| 2003/0084904 A1 | 5/2003 | Gunaratnam | |
| 2004/0079375 A1 | 4/2004 | Lithgow et al. | |
| 2004/0226566 A1 | 11/2004 | Gunaratnam et al. | |
| 2006/0231102 A1 * | 10/2006 | Bordewick et al. | 128/207.11 |
| 2009/0173343 A1 * | 7/2009 | Omura et al. | 128/202.27 |

FOREIGN PATENT DOCUMENTS

| | | | |
|---|---|---|---|
| JP | 2003-1903308 A | 7/2003 | |
| WO | 00/78384 | 12/2000 | |
| WO | WO 01/32250 | * 5/2001 | A61M 16/06 |

OTHER PUBLICATIONS

Office Action issued Jul. 3, 2009 in Chinese Patent Application No. 200580021230.5 (w/English translation).

Office Action issued in Japanese Appln. No. 2007-516895 (Aug. 24, 2010) w/English translation.

Office Action issued in European Appln. No. 05753870.4 (Jul. 19, 2010).

Supplementary Search Report issued in European Appln. 05753870. 4, dated Dec. 15, 2009.

International Search Report for PCT/AU2005/000931 mailed Jul. 19, 2005.

International Preliminary Report on Patentability, PCT/AU2005/000931 (Dec. 28, 2006).

* cited by examiner

FOREHEAD SUPPORT FOR A PATIENT INTERFACE

CROSS-REFERENCE TO APPLICATIONS

This application claims the benefit of U.S. Provisional Application No. 60/582,538, filed Jun. 25, 2004, which is incorporated herein by reference in its entirety.

FIELD OF THE INVENTION

The invention relates to a patient interface used for treating sleep disordered breathing. In particular, the invention relates to a forehead support for a patient interface.

BACKGROUND OF THE INVENTION

In the treatment of sleep disordered breathing, a patient receives a supply of air or breathable gas at positive pressure to "splint" open their airway. The supply of air or gas is delivered to the patient via a patient interface, such as a facial mask. The patient interface is typically held in position by headgear. Headgear typically includes a number of straps that in use are attached to the patient interface at an anchor point. In use, the various straps are tightened to secure the mask in position and to prevent it from lifting off the face under pressure. Generally, the higher the treatment pressure, the tighter the mask strap needs to be. When poorly fitting masks are used, patients sometimes over tighten the straps to try to get a seal. This can lead to pressure sores on their face. It is a continuing challenge for designers and manufacturers to provide a patient interface with comfortable seal against leak.

The addition of a forehead support to a facial mask can assist in stabilising the mask and provide a convenient means to adjust the mask to suit each patient. Improving the fit of the mask can lead to improved comfort, reduced noise and a more effective therapy.

Other known arrangements are found in U.S. Pat. Nos. 6,422,238 and 6,536,435 and Australian Patent Application AU 200071882 A1.

SUMMARY OF THE INVENTION

In accordance with a first aspect of the invention there is provided a patient interface comprising a cushion adapted to be positioned in use against a patient's face at an angle and an adjustable support wherein adjustment of the support adjusts the angle which the cushion makes with the patient's face.

In accordance with a second aspect of the invention there is provided a patient interface comprising a cushion adapted to be positioned in use against a patient's face at an angle and an adjustable forehead support wherein adjustment of the support adjusts the angle which the cushion makes with the patient's face.

In accordance with yet a further aspect of the invention there is provided a patient interface assembly comprising (i) a mask interface including a forehead support with an adjustment mechanism and (ii) headgear including at least one head strap attached to the forehead support wherein adjustment of the adjustment mechanism of the forehead support relocates said at least one strap to a different position on the head.

In accordance with another aspect of the invention, there is provided a generally "Y"-shaped forehead support for a facial mask.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE FIGURES

The accompanying drawings facilitate an understanding of the various embodiments of this invention. In such drawings.

DETAILED DESCRIPTION OF ILLUSTRATED EMBODIMENTS

Figure 1:
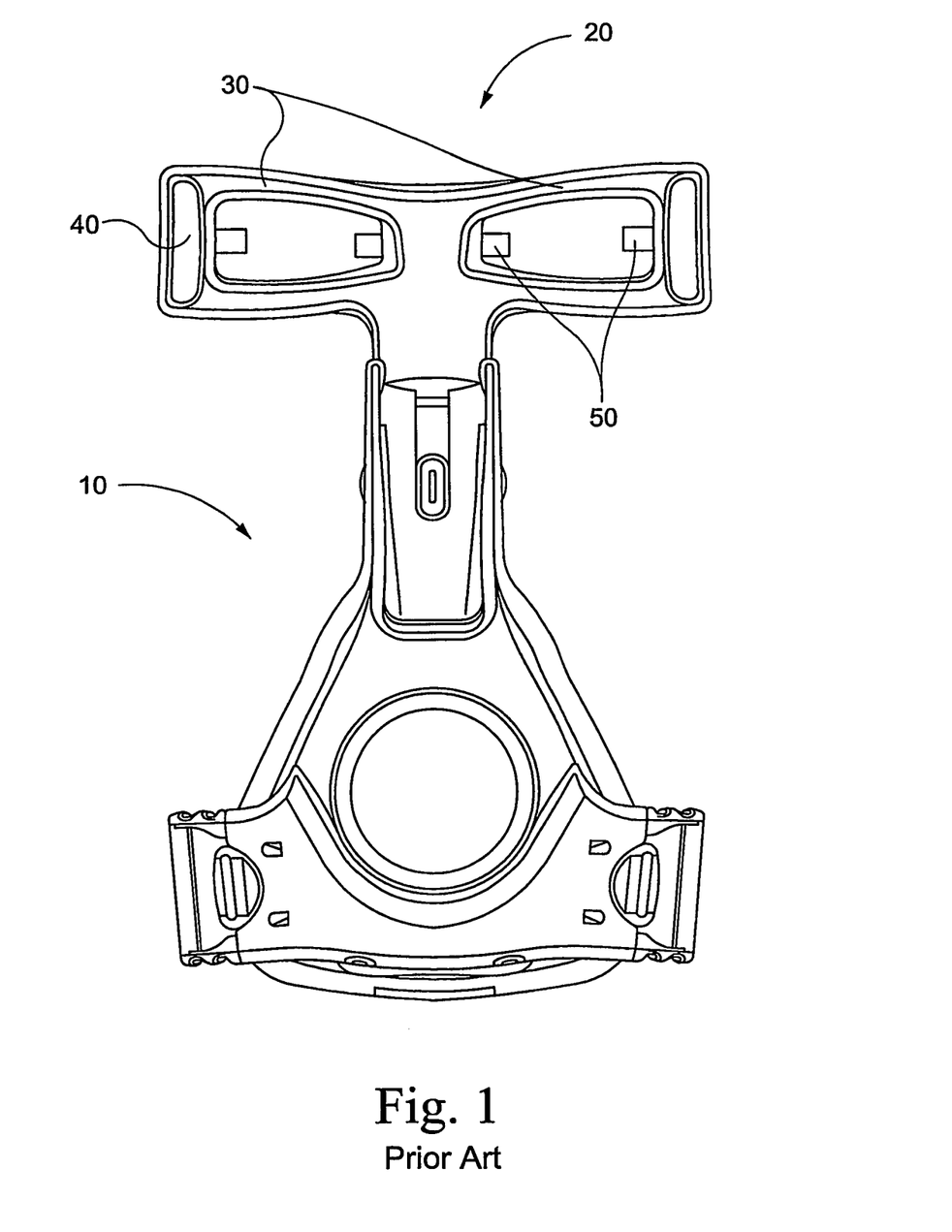
FIG. 1 shows a front view of a prior art frame for an ULTRA MIRAGE® mask.
Figure 2:
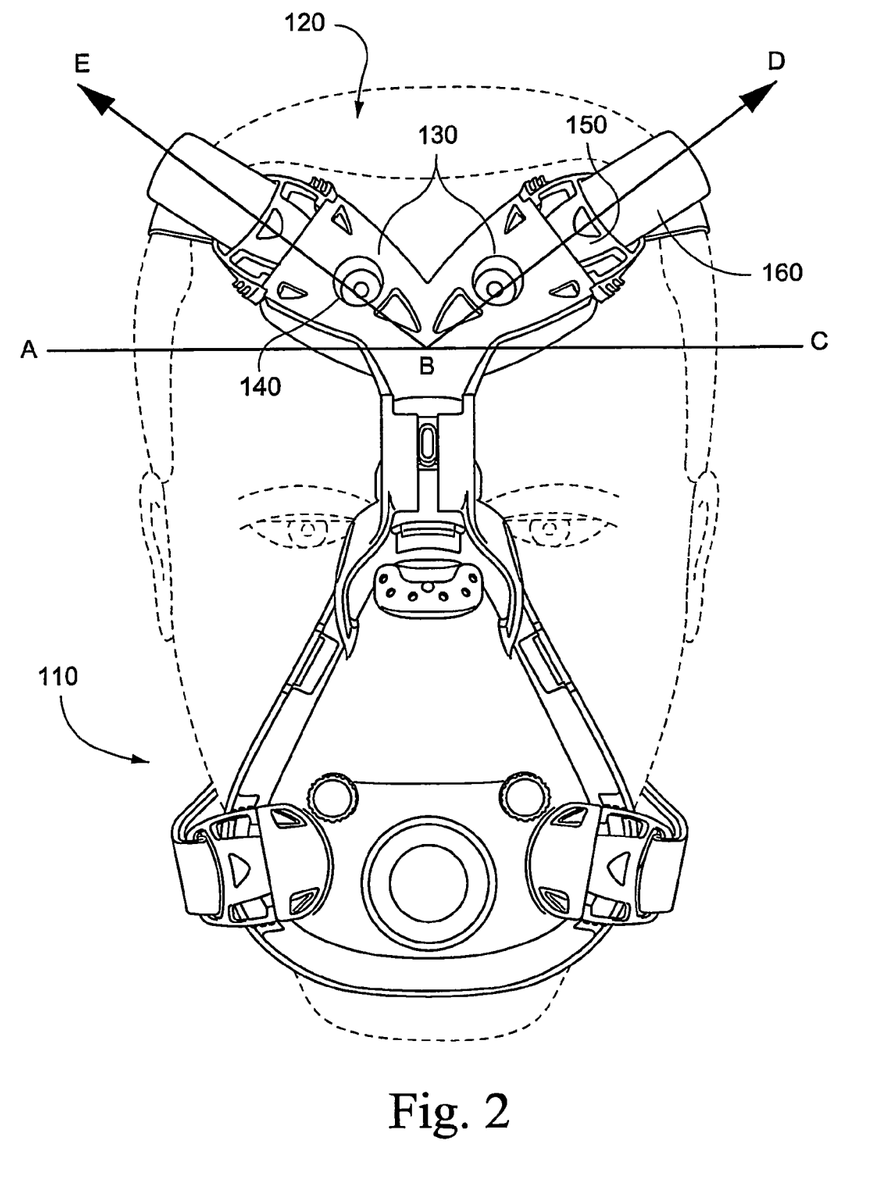
FIG. 2 shows a front view of a mask and forehead support assembly in accordance with a first embodiment of the invention on a glass head.

A prior art mask assembly 10 such as ResMed's ULTRA MIRAGE® mask as shown in FIG. 1 includes a forehead support 20 having a pair of arms 30, each having a slot 40 adapted to receive a strap (not shown). Each arm 30 includes a pair of forehead pad receiving lugs 50. The forehead support has a general "T"-shape, with the arms arranged along the upper cross portion of the "T":

As shown in FIG. 2, a mask assembly 110 in accordance with a first aspect of the invention provides a forehead support 120 including a pair of arms 130 defining an included angle EBD of less than 180°, for example 100°-150°, preferably 120°. Thus the forehead support is generally "Y"-shaped. In the embodiment shown in FIG. 2, each arm includes a slot arrangement 140 adapted to receive a forehead support clip 150. Each forehead support clip 150 is in turn adapted to engage with a forehead support strap 160. There is a line of force BE and BD for the respective arms 130.

Figure 3:
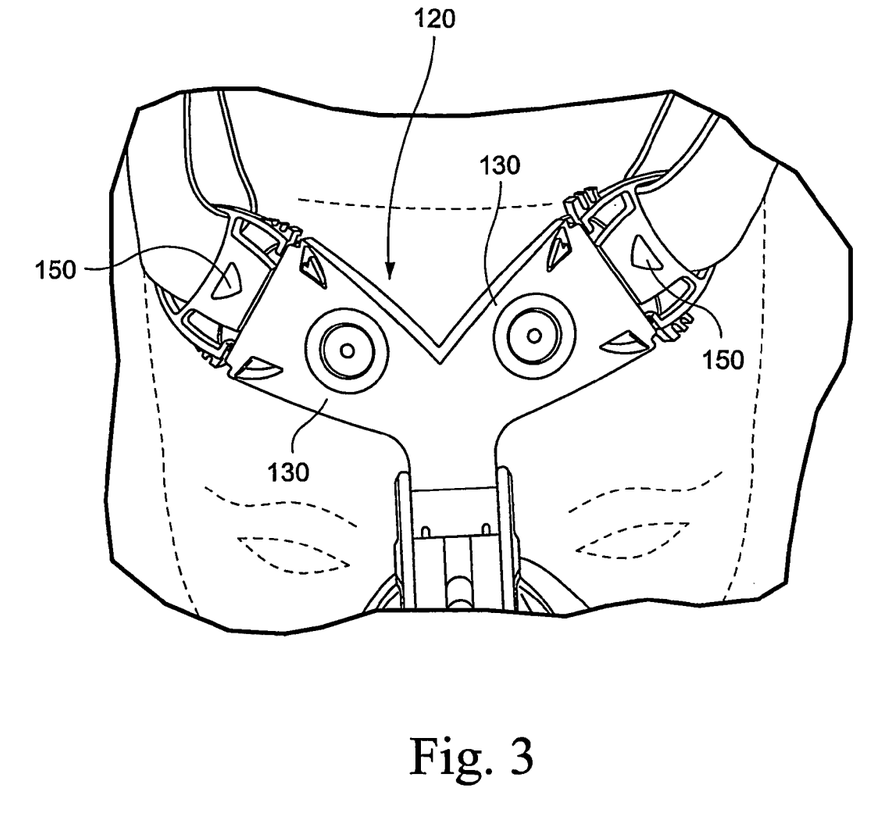
FIG. 3 shows a detail of the assembly of FIG. 2.

Each arm 130 is disposed at an angle (ABE or CBD) with respect to horizontal line ABC, that is, e.g., about 15°-40°, preferably 30°. However, the angle (ABE or CBD) may have any other suitable size, e.g., about 20°-80°, preferably about 40°-50°, or more preferably about 45°. The lines of force have a component in a vertical direction (with respect to the orientation depicted in FIG. 2, i.e., with the patient sitting upright), as opposed to being purely in a horizontal direction (as in the prior art). A feature of this arrangement is that when the straps are tightened they will pull the mask up the face, not just pulling the forehead support more tightly onto the face. FIG. 3 is an enlarged view of a portion of mask 120 shown in FIG. 3.

Figure 4:
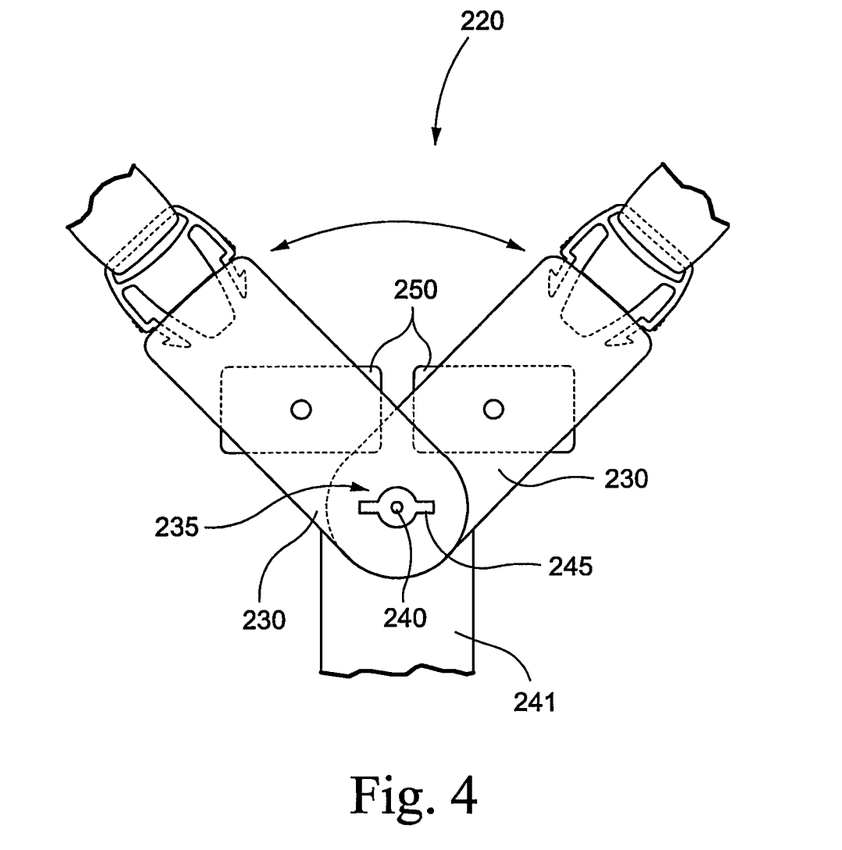
FIG. 4 shows an adjustable "Y"-shaped forehead support according to another embodiment of the invention.

In accordance with another aspect of the invention, the angle between the arms may be adjustable over a range of about 240°, e.g., where a first arm is positioned at about −30° and the second arm is positioned at about 210°. However, the preferable range of angles between the arms is as described above, the difference being that in the embodiment of FIGS. 2-3, angle is fixed while the angle of FIG. 4 is adjustable over the range. The arms can be positioned above or below horizontal, but are preferably above horizontal. In one form, this is achieved by an adjustable forehead support 220 in which each arm 230 has a hole 235 at one end. In use, a bolt 240 passes through both holes and a corresponding hole in a support post 241. The arms 230 are free to rotate with respect to the support post. A wing nut 245 on the end of the bolt 240 can be used to secure the arms when they have been adjusted to the desired angle. Each arm 230 is adapted to support a forehead pad 250.

Figure 5A:
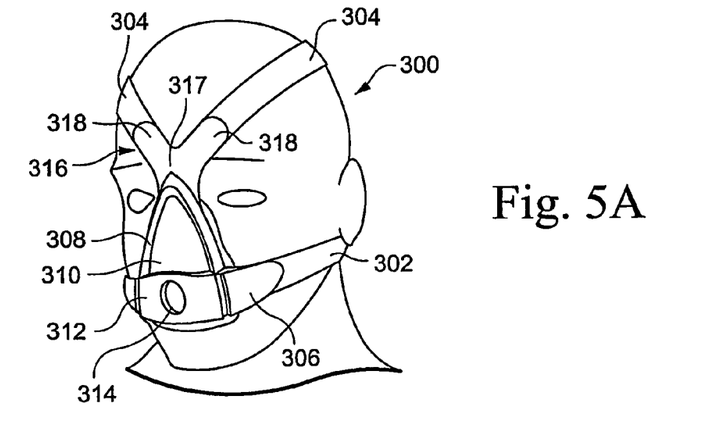
FIGS. 5A-5C show an alternative embodiment according to the present invention.
Figure 5B:
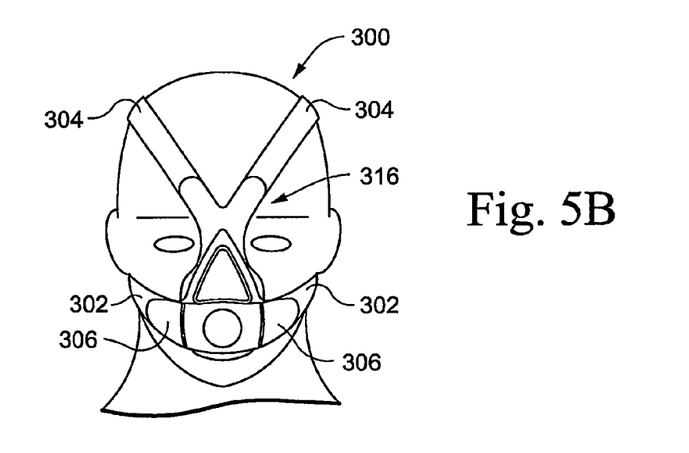
Figure 5C:
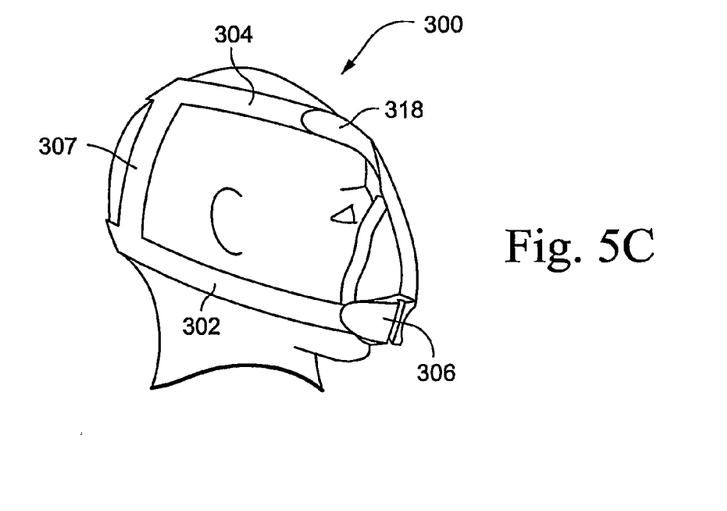

FIGS. 5A-5C illustrate another mask assembly 300 according to the present invention. Mask assembly 300 includes a pair of lower headgear straps 302 and a pair of upper headgear straps 304. The lower straps 302 are connected to a frame 308 via a pair of clips 306, which operate in a manner which is similar to that of clips 150 (described above). Frame 308 is adapted to support a cushion 310, which in this case is a full face cushion, although support frame 308 could be adapted to support a nasal cushion instead. Frame 308 includes a front plate 312 including an aperture 314 adapted to receive pressurized gas from an air delivery tube, e.g., via a swivel elbow.

Frame 308 is provided with a substantially Y-shaped extension including a base 317 and two upwardly extending arms 318. The arms 318 are disposed such that an angle between the arms is in the range of 30°-120°, and preferably about 70°-90°. The arms 318 may be connected to upper strap portion 304 via stitching, adhesives or other suitable fasteners.

The Y-shaped forehead support 316 is shown in this embodiment as being an integral part of frame 308. However, the base 317 of the support 316 could be structured such that it snap-fits or is otherwise detachably connectable to frame 308.

FIGS. 5B and 5C show, respectively, front and side views of the mask assembly 300 shown in FIG. 5A. As shown in FIG. 5C, the headgear includes a pair of rear headgear straps 307 which connect the lower and upper strap portions 302, 304 on each side of the patient's head in use.

Figure 6A:
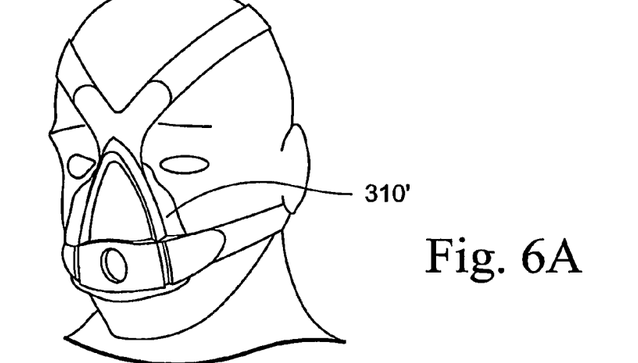
FIGS. 6A-6C show still another embodiment according to the present invention.
Figure 6B:
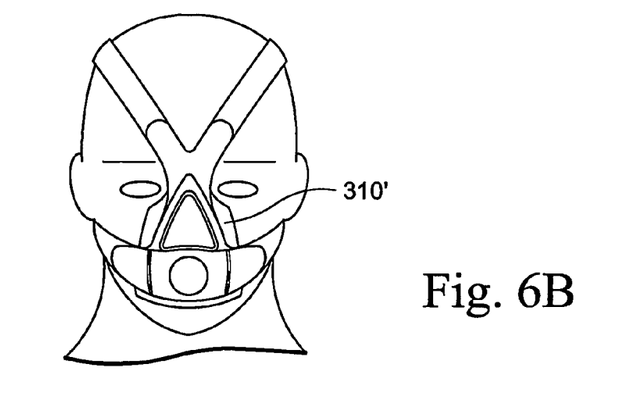
Figure 6C:
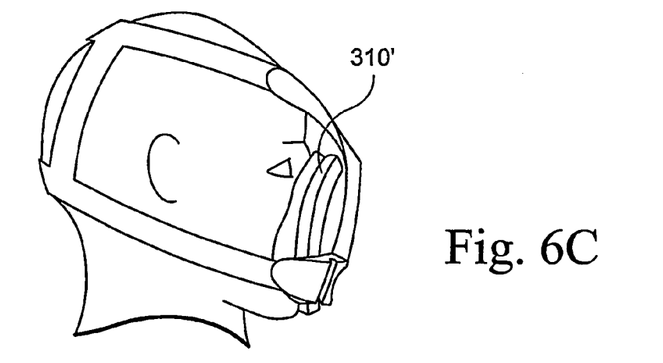

FIGS. 6A-6C illustrate still another embodiment of the present invention which is similar to the embodiment shown in FIGS. 5A-5C. However, FIGS. 6A-6C include a frame which supports a cushion 310' having a gusseted portion (as best seen in FIG. 6C). Operation of the gusseted portion is more fully described in U.S. patent application Ser. No. 09/885,445, filed Jun. 21, 2001, incorporated herein by reference in its entirety.

Figure 7:
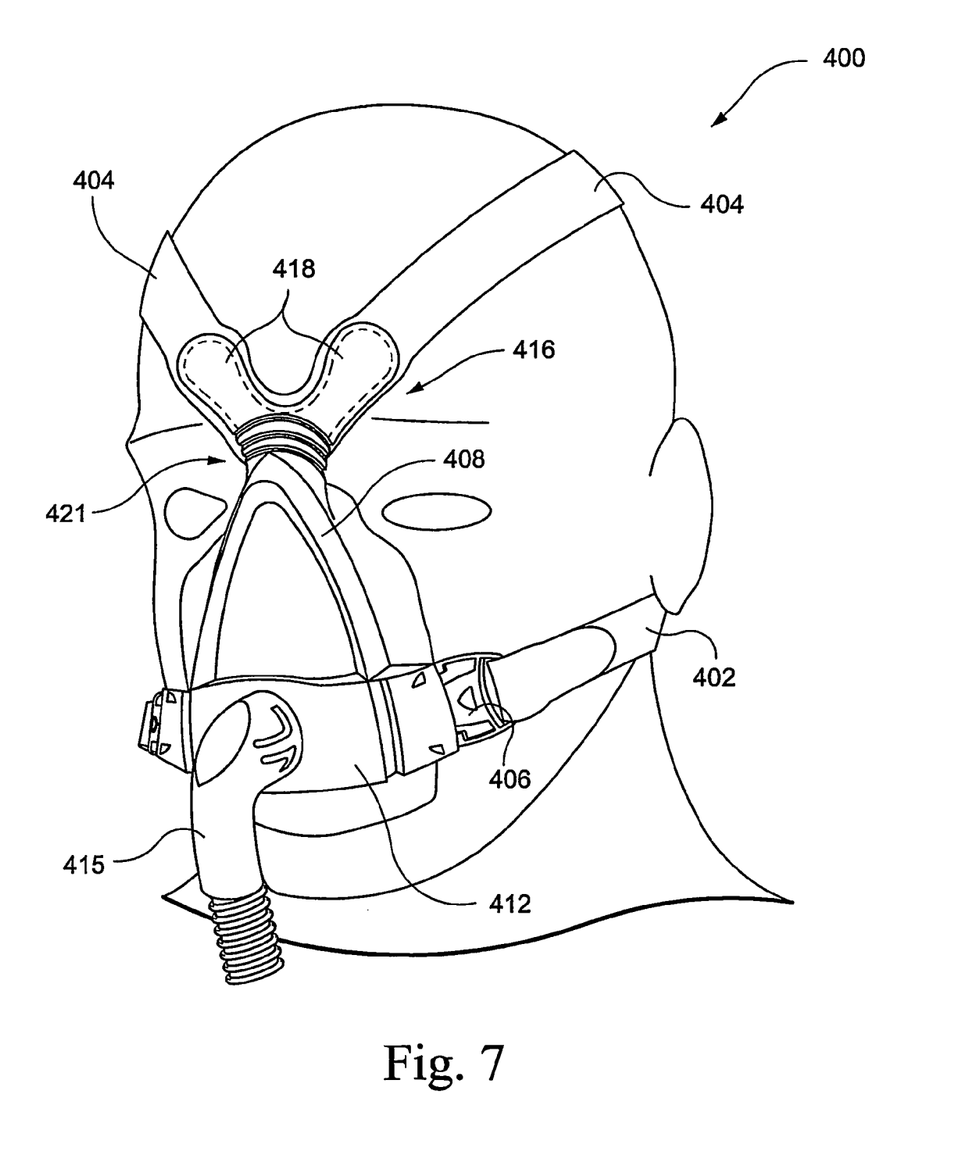
FIG. 7 shows yet another embodiment according to the present invention.

FIG. 7 is a perspective view of a mask assembly 400 according to still another embodiment of the present invention. Mask assembly 400 is like the assembly shown in FIGS. 5A-5C and/or 6A-6C, wherein like reference numbers indicate like parts. As shown in FIG. 7, an air delivery hose is provided to plate 412.

Forehead support 416 includes a flexible joint 421 which allows the forehead support 416 to angle the upwardly extending arm portions 418 in accordance with the slope of the patient's forehead.

Figure 8:
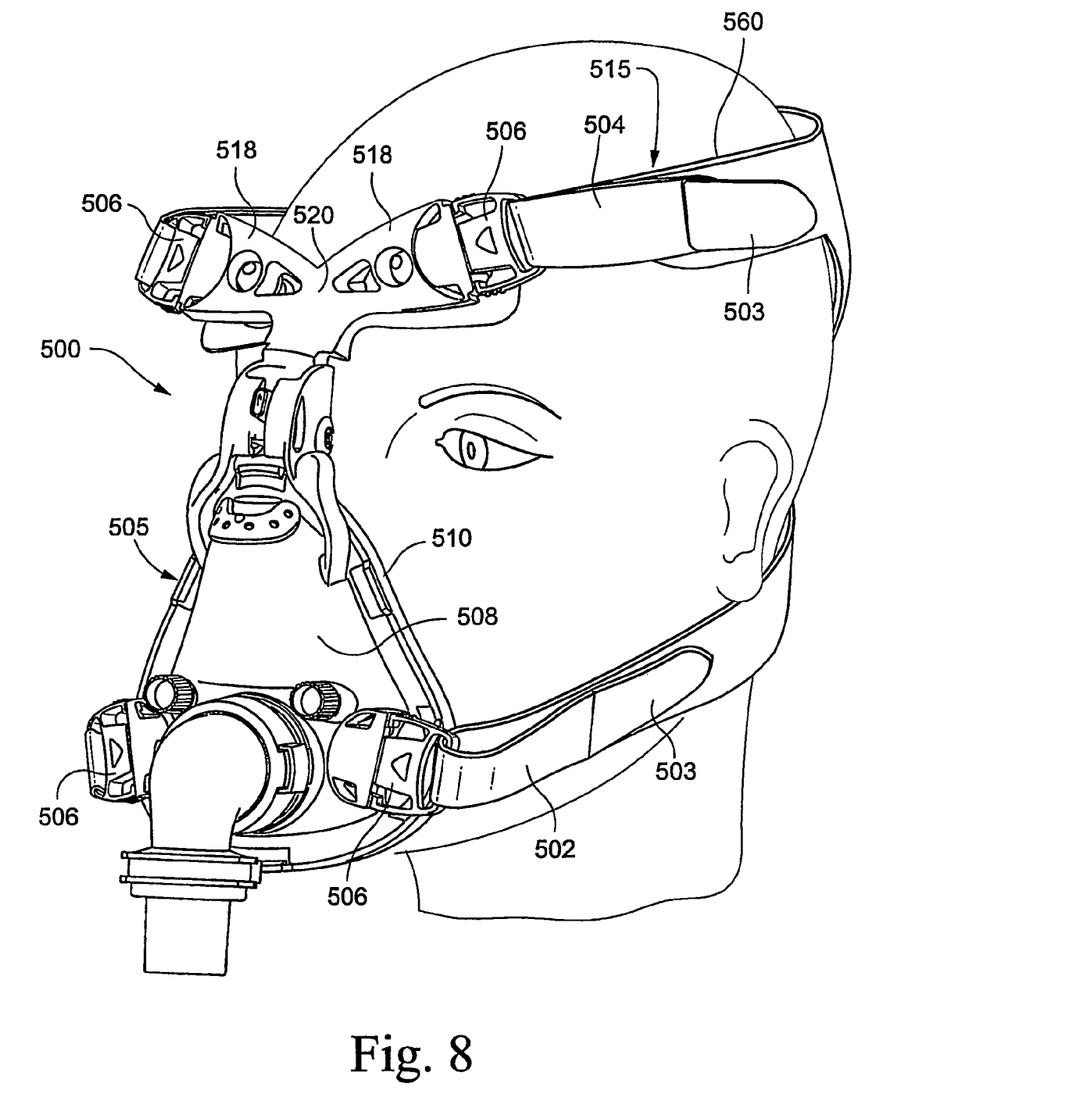
FIG. 8 is a side perspective view of a mask assembly according to yet another embodiment of the present invention on a patient's head.

FIGS. 8-12 illustrate a mask assembly 500 according to yet another embodiment of the present invention. As best shown in FIG. 8, the mask assembly 500 includes a mask 505 and headgear 515 to support the mask 505 on the patient's face. In the illustrated embodiment, the mask 505 is a full-face mask similar to the mask shown in FIG. 2 including a Y-shaped forehead support 520. Each arm 518 of the forehead support 520 is disposed at an angle with respect to horizontal, e.g., about 45°. However, each arm 518 may be disposed at other suitable angles as described above. Also, the mask 505 includes a frame 508 adapted to support a cushion 510, which in this case is a full face cushion, although the frame 508 may be adapted to support other suitable cushions, e.g., a nasal cushion. Also, the cushion 510 may include a gusseted portion as described above.

Figure 9:
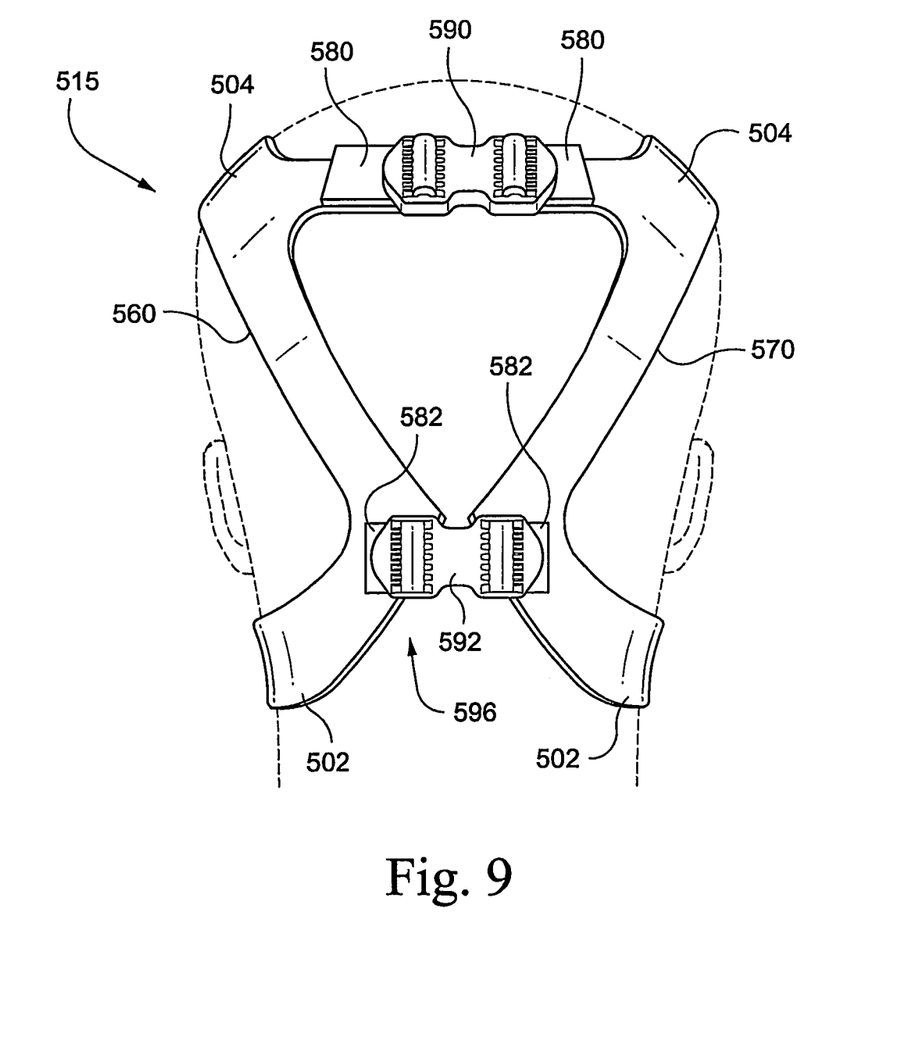
FIG. 9 is a rear view of the mask assembly shown in FIG. 8 on a patient's head.
Figure 10:
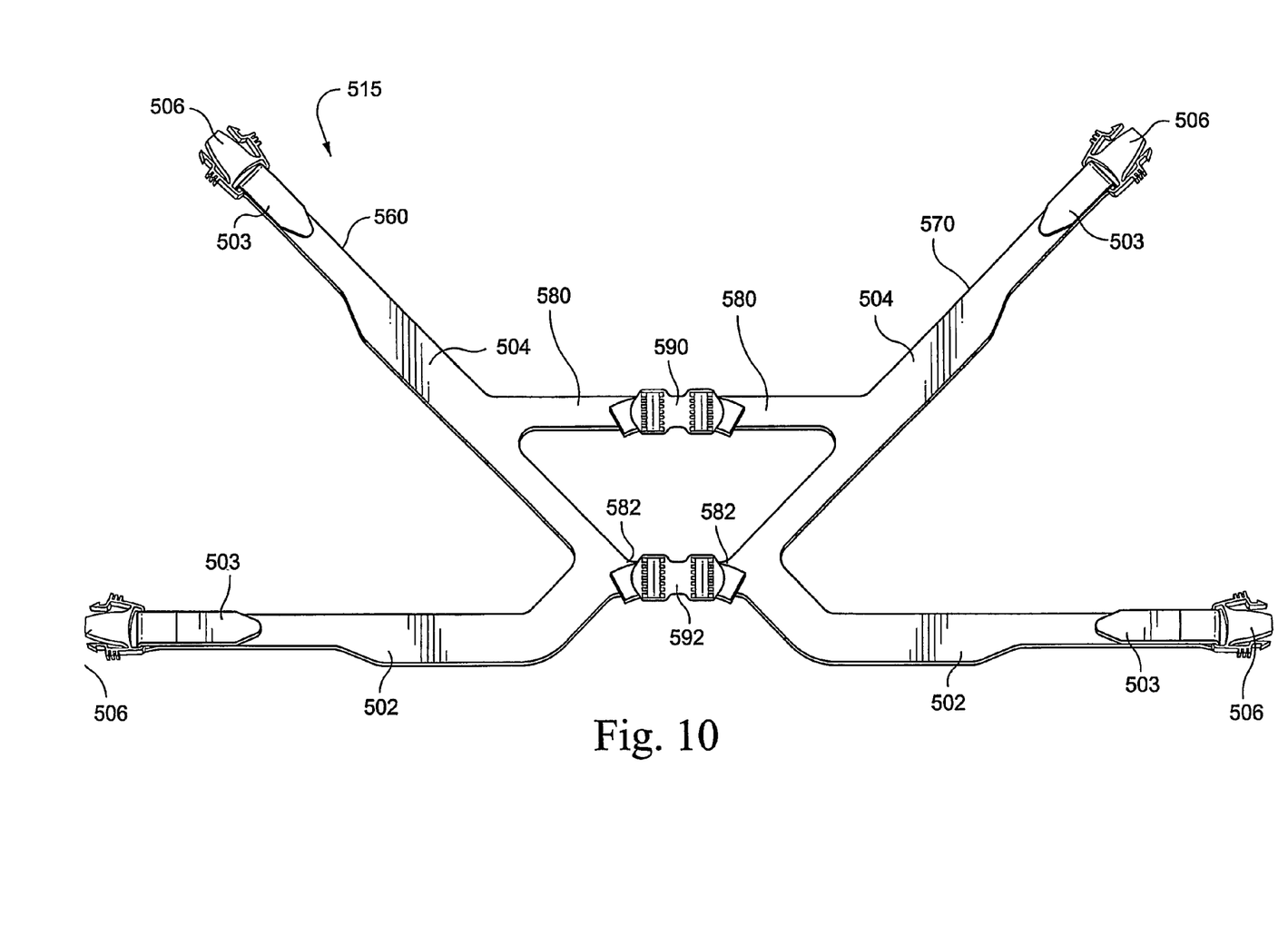
FIG. 10 is a top view of a headgear of the mask assembly shown in FIG. 8 removed from the mask and the patient's head.

As best shown in FIGS. 9 and 10, the headgear 515 includes a first side portion 560 and a second side portion 570 that is attached to the first side portion 560. The first and second side portions 560, 570 are substantially symmetrical to one another. This arrangement may achieve better or more efficient material use in manufacture. Each side portion 560, 570 includes an upper side strap 504 that is removably connected to a respective arm 518 of the Y-shaped forehead support 520, and a lower side strap 502 that that is removably connected to a lower portion of the mask frame 508. Also, each side portion 560, 570 includes an upper connecting strap 580 and a lower connecting strap 582.

The first and second side portions 560, 570 are attached to one another by attaching the upper connecting straps 580 of respective side portions 560, 570 to one another and attaching the lower connecting straps 582 of respective side portions 560, 570 to one another. In the illustrated embodiment, the upper connecting straps 580 are attached to one another via an upper ladder lock buckle 590, and the lower connecting straps 582 are attached to one another via an lower ladder lock buckle 592. In an embodiment, the ladder lock buckles 590, 592 may have a similar form to those disclosed in U.S. patent application Ser. No. 10/781,929, filed Feb. 20, 2004, the contents of which are hereby incorporated by reference in its entirety. However, the first and second side portions 560, 570 may be attached to one another in other suitable manners, e.g., stitched, welded, glued or otherwise formed, to form the headgear 515.

In the illustrated embodiment, the upper side straps 504 are removably connected to respective arms 518 of the Y-shaped forehead support 520 via clips 506, which operate in a manner similar to the clips described above. Also, the lower side straps 502 are removably connected to a lower portion of the mask frame 508 via clips 506. The free end of each of the upper and lower side straps 504, 502 includes a strip of Velcro® material 503 for use in securing each of the straps 504, 502 to a respective clip 506. FIGS. 8 and 9 illustrate the headgear 515 attached to the mask 505 and secured on the patient's head, and FIG. 10 illustrates the headgear 515 removed from the mask 505 and the patient's head. However, the upper and lower side straps 504, 502 may be attached to mask 505 in other suitable manners.

When the headgear 515 is secured on the patient's head, the two upper side straps 504 are angled about 45° with respect to horizontal to achieve desired force vectors similar to FIG. 2. As described above, this arrangement generates both horizontal and vertical force vectors such that when the straps 504 are tightened they will pull the mask up the face, not just pulling the forehead support 520 more tightly onto the face. This assists with better positioning of the mask 505 on the patient's face and stops the mask 505 from falling down the patient's face, especially with increased weight of full face gusseted cushion. Also, as shown in FIG. 9, the lower connecting straps 582 are configured such that they provide an increased cutaway 596 at the lower rear of the patient's head. This arrangement prevents the headgear 515 from sitting on soft tissue at the back of the patient's head or neck. This arrangement also prevents the headgear 515 from "digging" into the lower edge of the patient's occipital bone.

In the illustrated embodiment, the upper ladder lock buckle 590 provides adjustment across the ball of the patient's head, i.e., around the base of the patient's parietal bone. The lower ladder lock buckle 592 is not intended to be adjusted, but only functions to assemble the two side portions 560, 570. However, the upper and lower ladder lock buckles 590, 592 may have other arrangements, e.g., both adjustable, both non-adjustable.

Figure 11:
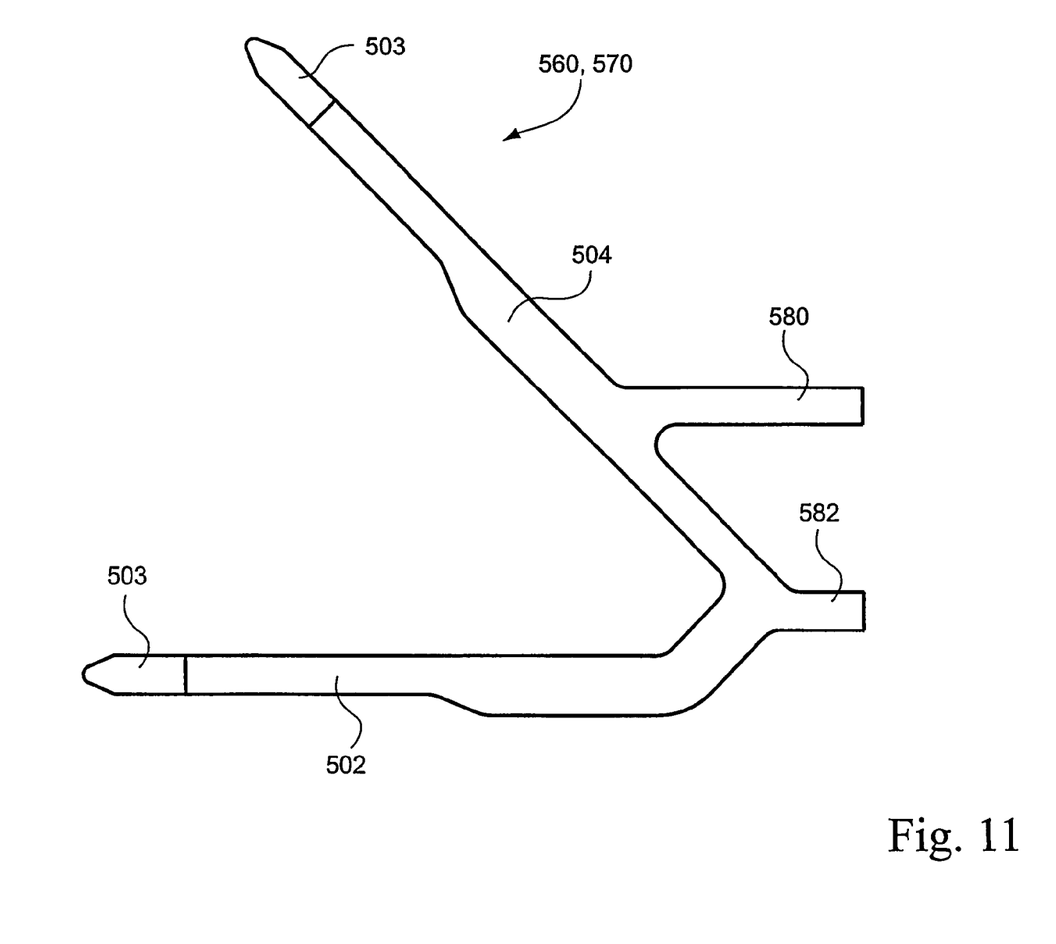
FIG. 11 is a plan view of a side portion of the headgear shown in FIG. 10.
Figure 12:
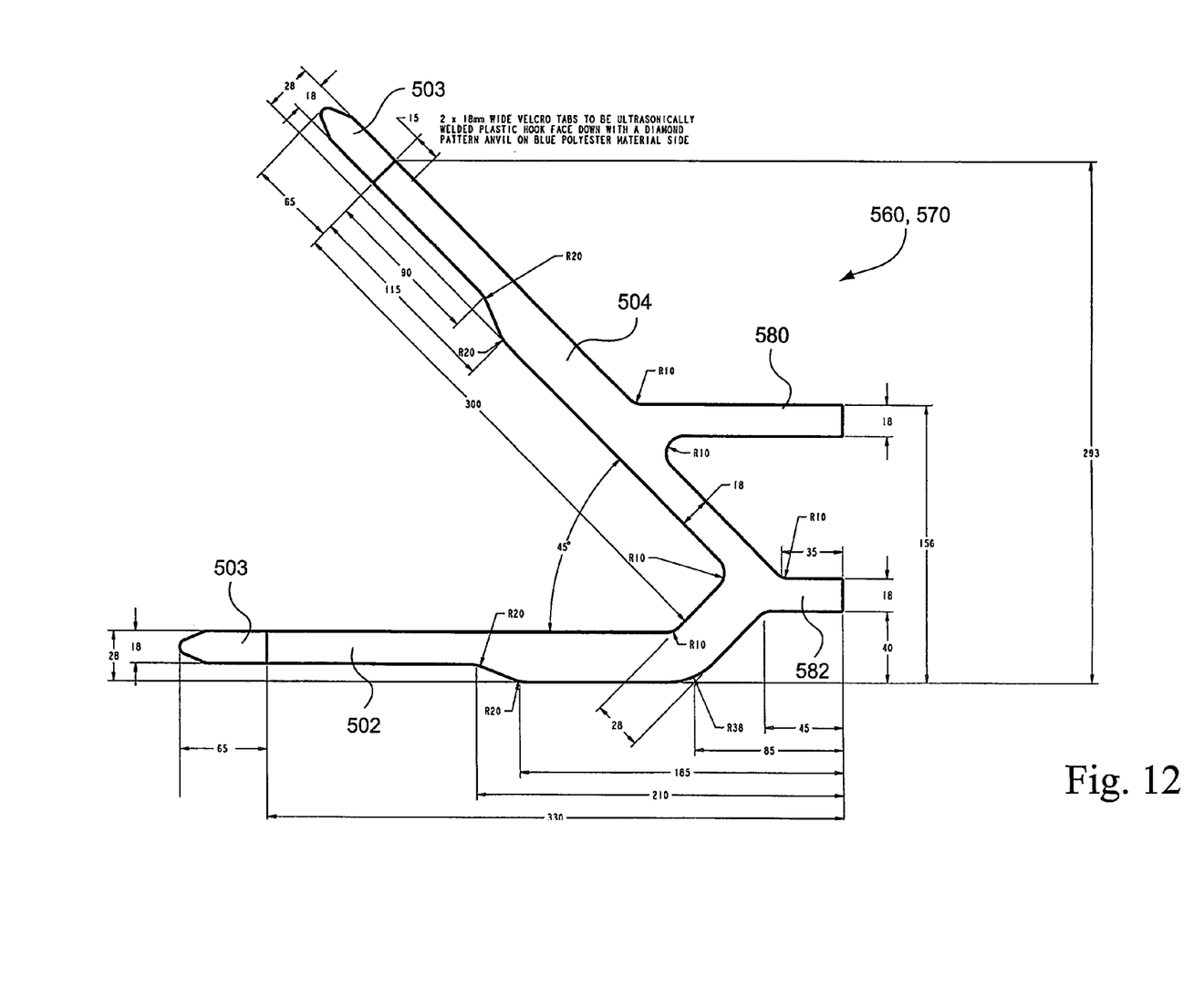
FIG. 12 is a plan view of the side portion shown in FIG. 11 and showing dimensions of an embodiment.

FIG. 11 illustrates an embodiment of a side portion 560, 570, and FIG. 12 illustrates dimensions of an embodiment of a side portion 560, 570. Although specific dimensions of a side portion 560, 570 are shown in FIG. 12, it is to be understood that these dimensions are merely exemplary and other dimensions are possible depending on application.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A mask assembly comprising:
   a frame to support a mask cushion;
   a headgear including a pair of lower straps and a pair of upper straps; and
   a forehead support comprising a base provided to the frame and a pair of arms extending upwardly from the base, each of the arms including a free end, and the free end of one of the pair of arms being spaced and separated from the free end of the other of the pair of arms, and each arm connected to a respective one of the pair of upper straps, wherein an angle between the spaced and separated arms, as seen in front view, is less than 180°,
   the forehead support further comprising a flexible joint provided as a separate and distinct structure positioned entirely above the frame and entirely below the pair of arms allowing the forehead support to self-adjust the arms in accordance with the slope of the patient's forehead without manual adjustment of the forehead support,
   wherein the frame and the forehead support are formed as an integral one piece unit.

2. The mask assembly according to claim 1, wherein the pair of upwardly extending arms define an included angle of about 40°-160°.

3. The mask assembly according to claim 1, wherein forehead support is Y-shaped.

4. The mask assembly according to claim 1, wherein an end of each arm is adapted to be connected to the headgear strap, the arm being structured to transmit a force from the headgear, the force having a component in both a horizontal direction and a vertical direction, adapted to pull the mask assembly up the patient's face.

5. The mask assembly according to claim 1, wherein the pair of upwardly extending arms define an included angle that is in the range of 100°-150°.

6. The mask assembly according to claim 1, wherein the cushion has a gusseted portion.

7. The mask assembly according to claim 1, wherein the frame includes a front plate including an aperture for receiving pressurized gas from an air delivery tube.

8. The mask assembly according to claim 1, wherein self-adjustment of the arms includes self-adjustment of an angle of the arms relative to the patient's forehead.

9. The mask assembly according to claim 1, wherein adjustment of the straps causes adjustment of the forehead support.

10. The mask assembly according to claim 1, wherein the flexible joint includes a gusseted portion.

11. The mask assembly according to claim 1, wherein the flexible joint includes a plurality of flexible portions.

12. The mask assembly according to claim 1, wherein the flexible joint includes a plurality of generally horizontally extending recesses.

13. The mask assembly according to claim 1, wherein the flexible joint provides a distinct location of flexion.

14. The mask assembly according to claim 13, wherein the flexible joint allows the pair of arms to flex to alter an angle between the pair of arms and the base.

15. The mask assembly according to claim 13, wherein the flexible joint includes a gusseted portion that provides the distinct location of flexion.

16. A mask assembly comprising:
    a frame to support a mask cushion;
    a headgear including a pair of lower straps and a pair of upper straps; and
    a forehead support comprising a base provided to the frame and a pair of arms extending upwardly from the base, each of the arms including a free end, and the free end of one of the pair of arms being spaced and separated from the free end of the other of the pair of arms, and each arm connected to a respective one of the pair of upper straps, wherein an angle between the spaced and separated arms, as seen in front view, is less than 180°,
    the forehead support further comprising a flexible joint provided as a separate and distinct structure positioned entirely above the frame and entirely below the pair of arms allowing the forehead support to self-adjust the arms in accordance with the slope of the patient's forehead without manual adjustment of the forehead support,
    wherein the flexible joint includes a gusseted portion.

17. The mask assembly according to claim 16, wherein the gusseted portion provides a distinct location of flexion.

18. The mask assembly according to claim 17, wherein the gusseted portion allows the pair of arms to flex to alter an angle between the pair of arms and the base.

19. A mask assembly comprising:
    a frame to support a mask cushion;
    a headgear including a pair of lower straps and a pair of upper straps; and
    a forehead support comprising a base provided to the frame and a pair of arms extending upwardly from the base, each of the arms including a free end, and the free end of one of the pair of arms being spaced and separated from the free end of the other of the pair of arms, and each arm connected to a respective one of the pair of upper straps, wherein an angle between the spaced and separated arms, as seen in front view, is less than 180°, the forehead support further comprising a flexible joint provided as a separate and distinct structure positioned entirely above the frame and entirely below the pair of arms allowing the forehead support to self-adjust the arms in accordance with the slope of the patient's forehead without manual adjustment of the forehead support, wherein the base is provided to an apex of the frame such that the flexible joint is positioned and arranged to provide a flexible region adjacent the apex of the frame.

20. The mask assembly according to claim 19, wherein the flexible joint provides a distinct location of flexion.

21. The mask assembly according to claim 20, wherein the flexible joint allows the pair of arms to flex to alter an angle between the pair of arms and the base.

22. The mask assembly according to claim 20, wherein the flexible joint includes a gusseted portion that provides the distinct location of flexion.

* * * * *

UNITED STATES PATENT AND TRADEMARK OFFICE
CERTIFICATE OF CORRECTION

PATENT NO.       : 8,695,601 B2
APPLICATION NO. : 11/630360
DATED            : April 15, 2014
INVENTOR(S)      : Hitchcock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1890 days.

Signed and Sealed this
Twenty-ninth Day of September, 2015

Michelle K. Lee
*Director of the United States Patent and Trademark Office*